US012605289B2

(12) United States Patent
Shiraki et al.

(10) Patent No.: US 12,605,289 B2
(45) Date of Patent: Apr. 21, 2026

(54) DETERMINATION DEVICE, DETERMINATION METHOD, AND DETERMINATION SYSTEM

(71) Applicant: SINTOKOGIO, LTD., Nagoya (JP)

(72) Inventors: Masataka Shiraki, Nagoya (JP);
Yoshihisa Suzuki, Nagoya (JP)

(73) Assignee: SINTOKOGIO, LTD., Aichi (JP)

( * ) Notice: Subject to any disclaimer, the term of this patent is extended or adjusted under 35 U.S.C. 154(b) by 294 days.

(21) Appl. No.: 18/475,668

(22) Filed: Sep. 27, 2023

(65) Prior Publication Data

US 2024/0139038 A1     May 2, 2024

(30) Foreign Application Priority Data

Oct. 26, 2022    (JP) ................................. 2022-171746

(51) Int. Cl.
*A61F 13/496*       (2006.01)
*A61F 13/42*        (2006.01)
(52) U.S. Cl.
CPC ............ *A61F 13/496* (2013.01); *A61F 13/42* (2013.01)

(58) Field of Classification Search
CPC ....... A61F 13/496; A61F 13/42; G01N 33/48; A61B 5/20; A61B 5/48; A61B 5/6805; A61B 5/6808; A61B 2560/0462
See application file for complete search history.

(56) References Cited

U.S. PATENT DOCUMENTS

2018/0311080 A1* 11/2018 Potter ..................... A61B 90/98

FOREIGN PATENT DOCUMENTS

CN          116158909 A  *  5/2023  ............. A61F 13/42
JP          2014-33745 A     2/2014
WO     WO-2012126507 A1 *  9/2012  ............. A61F 13/44

* cited by examiner

*Primary Examiner* — Susan S Su
(74) *Attorney, Agent, or Firm* — Harness, Dickey & Pierce, P.L.C.

(57)          ABSTRACT
In order to provide a novel determination device capable of determining the type of excretion by a subject and a related technology thereof, a determination device includes at least one processor, and the at least one processor carries out a determination process of determining the type of excretion by a subject by referring to a first gas concentration, which is a gas concentration detected by a first gas sensor, and a second gas concentration, which is a gas concentration detected by a second gas sensor that is disposed at a position farther from the subject than a position at which the first gas sensor is disposed.

5 Claims, 3 Drawing Sheets

START

Acquisition process ～M11

Determination process ～M12

Notification process ～M13

END

DETERMINATION DEVICE, DETERMINATION METHOD, AND DETERMINATION SYSTEM

This Nonprovisional application claims priority under U.S.C. § 119 on Patent Application No. 2022-171746 filed in Japan on Oct. 26, 2022, the entire contents of which are hereby incorporated by reference.

TECHNICAL FIELD

The present invention relates to a determination device, a determination method, and a determination system each of which is for determining a type of excretion.

BACKGROUND ART

In care services or medical services, excretion management for service users is one of important operations. If automatic detection of excretion of the service users, including automatic detection of a type of the excretion, is possible, a burden of the excretion management on service providers can be significantly reduced.

As a technique for detecting excretion of a service user, for example, the technique disclosed in Patent Literature 1 has been known. The technique disclosed in Patent Literature 1 determines, on the basis of an output signal from an odor sensor and an output signal from a humidity sensor, a type of excreta of a care receiver and whether leakage from a diaper of the care receiver occurs and then notifies a caregiver of a degree of urgency of treatment for the excretion.

CITATION LIST

Patent Literature

[Patent Literature 1]
  Japanese Patent Application Publication, Tokukai, No. 2014-33745

SUMMARY OF INVENTION

Technical Problem

The technique disclosed in Patent Literature 1 is a technique of determining a type of excreta by referring to a combination of a signal from the odor sensor and a signal from the humidity sensor. Unfortunately, in the technique disclosed in Patent Literature 1, used are the odor sensor, the humidity sensor, and a suction fan, and thus a determination system may have a complicated structure.

An aspect of the present invention is achieved in light of the foregoing problem. It is an object of the aspect of the present invention to provide a novel determination device capable of determining the type of excretion by a subject and a related technology thereof.

Solution to Problem

A determination device in accordance with an aspect of the present invention includes at least one processor, the at least one processor being configured to carry out a determination process of determining a type of excretion by a subject by referring to a first gas concentration and a second gas concentration, the first gas concentration being a gas concentration detected by a first gas sensor, the second gas concentration being a gas concentration detected by a second gas sensor which is disposed at a position farther from the subject than a position at which the first gas sensor is disposed.

A determination method in accordance with an aspect of the present invention includes: an acquisition process of at least one processor acquiring a first gas concentration and a second gas concentration, the first gas concentration being a gas concentration detected by a first gas sensor, the second gas concentration being a gas concentration detected by a second gas sensor which is disposed at a position farther from a subject than a position at which the first gas sensor is disposed; and a determination process of the at least one processor determining a type of excretion by the subject by referring to the first gas concentration and the second gas concentration.

A determination system in accordance with an aspect of the present invention includes: a first gas sensor; a second gas sensor disposed at a position farther from a subject than a position at which the first gas sensor is disposed; and a determination device configured to carry out a determination process of determining a type of excretion by the subject by referring to a first gas concentration and a second gas concentration, the first gas concentration being a gas concentration detected by the first gas sensor, the second gas concentration being a gas concentration detected by the second gas sensor.

Advantageous Effects of Invention

An aspect of the present invention makes it possible to provide a novel determination device capable of determining a type of excretion by a subject and a related technology thereof.

DESCRIPTION OF EMBODIMENTS (Configuration of Determination System)

Figures 1, 2:
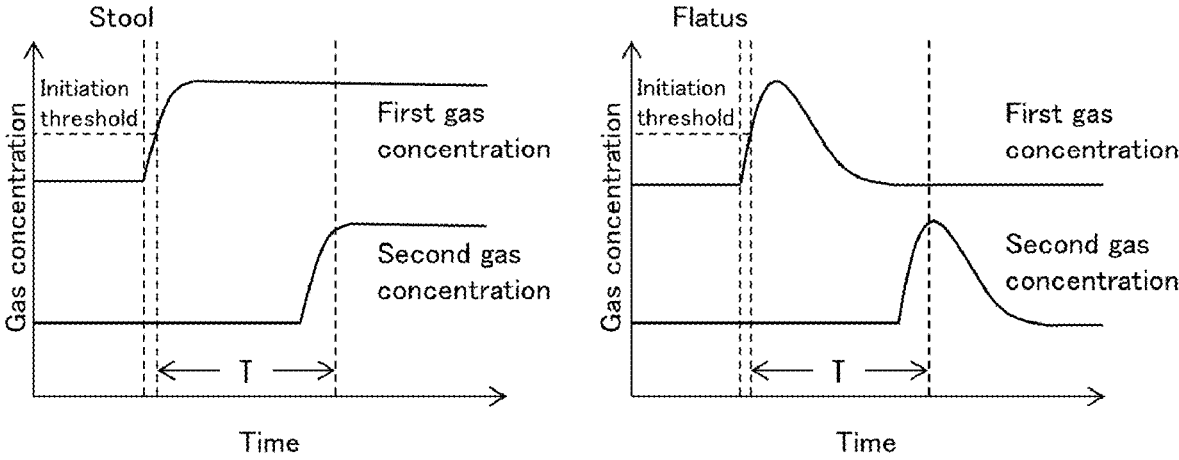
FIG. 1 is a view schematically illustrating a configuration of a determination system in accordance with an embodiment of the present invention.
FIG. 2 is graphs each schematically showing changes in first gas concentration and second gas concentration in a case where a stool or flatus occurs, in an embodiment of the present invention.

With reference to FIG. 1, the following will describe a determination system S in accordance with an embodiment of the present invention. FIG. 1 is a view schematically illustrating a configuration of the determination system S in accordance with an embodiment of the present invention.

The determination system S is a system configured to, in facilities for providing care services and/or medical services, determine a type of excretion by a service user Ua who is a subject and notify a service provider Ub of a result of the determination. In the present embodiment, the type of the excretion is determined to be either one of a stool or flatus. Note that, in the present specification, the "flatus" means a phenomenon in which a gas is discharged from a body without defecation. The "flatus" does not include a phenomenon in which a gas is discharged from a body during defecation, a phenomenon in which a gas is discharged from a stool after defecation, and a phenomenon in which a gas is discharged from urine after urination.

As illustrated in FIG. 1, the determination system S includes a determination device 1, a notification terminal 2, a relay terminal 3, a first gas sensor 41, and a second gas sensor 42. The determination device 1 and the notification terminal 2 communicate with each other via a network. The determination device 1 and the relay terminal 3 communicate with each other via a network. The relay terminal 3 and each of the first gas sensor 41 and the second gas sensor 42 communicate with each other without using any network (communicate with each other via, for example, near field wireless communication).

The first gas sensor 41 is attached to the service user Ua. As an example, the first gas sensor 41 is attached to the inside of underwear (diaper, underpants, panties, or the like) of the service user Ua. The first gas sensor 41 transmits an output signal therefrom to the determination device 1 via the relay terminal 3. The first gas sensor 41 includes a processor and a communication interface, and the processor performs communication from the first gas sensor 41 to the relay terminal 3 with use of the communication interface.

The second gas sensor 42 is disposed at a position farther from the service user Ua than a position at which the first gas sensor 41 is disposed. The position of the second gas sensor 42 is determined, for example, with respect to a hip of the service user Ua. As an example, the second gas sensor 42 is attached to the inside of upper garment (pajama top, sweater, or the like) of the service user Ua. The second gas sensor 42 includes a processor and a communication interface, and the processor performs communication from the second gas sensor 42 to the relay terminal 3 with use of the communication interface. Hereinafter, in the present specification, a simple term "gas sensor(s)" means both of or either one of the first gas sensor 41 and the second gas sensor 42.

The first gas sensor 41 is configured to selectively detect a predetermined gas species. In addition, the second gas sensor 42 is configured to selectively detect the same gas species as the gas species to be selectively detected by the first gas sensor 41. That is, the first gas sensor 41 and the second gas sensor 42 mainly detect the same gas species. In the present embodiment, the first gas sensor 41 and the second gas sensor 42 are hydrogen sulfide sensors. In the present specification, a concentration of gas detected by the first gas sensor 41 is referred to as "first gas concentration", and a concentration of gas detected by the second gas sensor 42 is referred to as "second gas concentration".

Note that, the present invention is not limited to the configuration in which the first gas sensor 41 and the second gas sensor 42 are the hydrogen sulfide sensors. The first gas sensor 41 and the second gas sensor 42 may be gas sensors configured to selectively detect the same gas species derived from a stool and may be sensors for selectively detecting, for example, hydrogen sulfide, methyl mercaptan, skatole, or indole. Alternatively, the first gas sensor 41 and the second gas sensor 42 may be gas sensors configured to selectively detect the same gas species derived from flatus and may be, for example, hydrogen sensors. Further alternatively, the first gas sensor 41 and the second gas sensor 42 may be gas sensors configured to selectively detect gas species different from each other.

An output signal from the first gas sensor 41 includes information indicating a time series of a first gas concentration, and an output signal from the second gas sensor 42 includes information indicating a time series of a second gas concentration. Hereinafter, for simple descriptions, the information indicating a time series of a first gas concentration and the information indicating a time series of a second gas concentration are simply referred to as "first gas concentration" and "second gas concentration", respectively.

Note that, in the following descriptions, for simplification, it is assumed that both flatus and a stool contain the gas species that the first gas sensor 41 and the second gas sensor 42 selectively detect. In this case, in a case where the excretion by the service user Ua is a stool, the first gas concentration and the second gas concentration change as indicated in a left graph shown in FIG. 2. In a case where the excretion by the service user Ua is flatus, the first gas concentration and the second gas concentration change as indicated in a right graph shown in FIG. 2.

The relay terminal 3 is disposed in the vicinity of the first gas sensor 41 and the second gas sensor 42. As an example, the relay terminal 3 is disposed in a room in which the service user Ua is present. The relay terminal 3 receives an output signal(s) from a gas sensor(s). Further, the relay terminal 3 transmits, to the determination device 1, the output signal(s) from the gas sensor(s) received. In the present embodiment, as the relay terminal 3, a smartphone is used. Alternatively, a stationary wireless relay device may be used as the relay terminal 3.

The determination device 1 is disposed outside the facility as described above. As an example, the determination device 1 is disposed in a data center. The determination device 1 receives, from the relay terminal 3, the output signal(s) from the gas sensor(s). Further, the determination device 1 determines a type of excretion by the service user Ua with reference to the output signal(s) from the gas sensor(s) received from the relay terminal 3. The determination device 1 then transmits a notification screen including a result of the determination to the notification terminal 2. Note that, for example, a computer disposed in the facility may be alternatively used as the determination device 1.

The notification terminal 2 is carried by the service provider Ub. The notification terminal 2 receives, from the determination device 1, data indicating the notification screen. In addition, the notification terminal 2 includes a display of a touch panel type and is configured to display the notification screen on the display on the basis of the data received from the determination device 1. In the present embodiment, as the notification terminal 2, a smartphone is used. Note that, in the following descriptions, transmitting data indicating a notification screen is described as transmitting the notification screen, and receiving data indicating each screen is described as receiving the screen.

(Configuration of Determination Device)

Figures 3, 4:
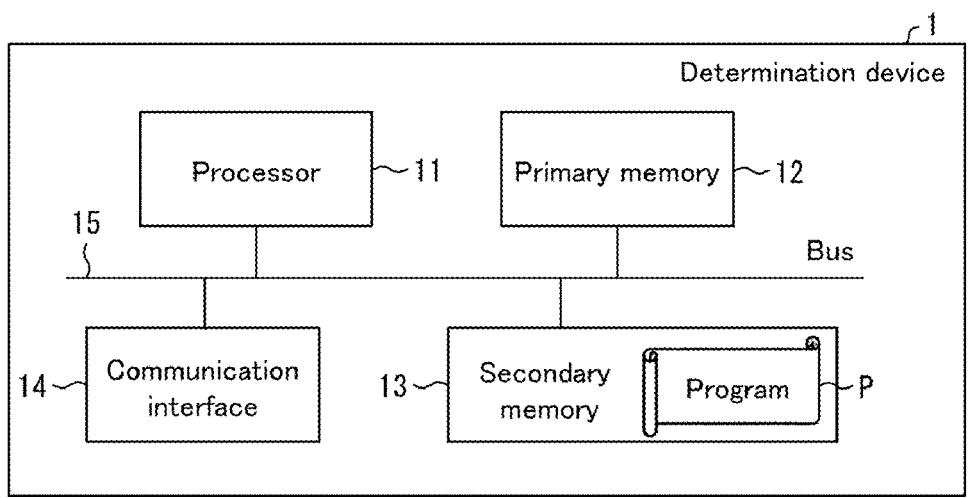
FIG. 3 is a block diagram illustrating a configuration of a determination device included in the determination system illustrated in FIG. 1.
FIG. 4 is a flowchart showing a flow of a determination method carried out by the determination device illustrated in FIG. 3.

With reference to FIG. 3, the following will describe the configuration of the determination device 1 included in the determination system S. FIG. 3 is a block diagram showing the configuration of the determination device 1 included in the determination system S illustrated in FIG. 1.

As illustrated in FIG. 3, the determination device 1 includes a processor 11, a primary memory 12, a secondary memory 13, a communication interface 14, and a bus 15. The processor 11, the primary memory 12, the secondary memory 13, and the communication interface 14 are connected with each other via the bus 15. Examples of a device usable as the determination device 1 include a workstation constituting a cloud server.

The secondary memory 13 stores a determination program P. The processor 11 loads, on the primary memory 12, the determination program P stored in the secondary memory 13. The processor 11 then carries out processes included in a determination method M1 (described later) in accordance with instructions included in the determination program P loaded on the primary memory 12. Examples of a device usable as the processor 11 include a central processing unit (CPU). Examples of a device usable as the primary memory 12 include a semiconductor random access memory (RAM). Examples of a device usable as the secondary memory 13 include a hard disk drive (HDD).

The communication interface 14 is an interface for communicating with the notification terminal 2 and the relay terminal 3 via a network. Examples of an interface usable as the communication interface 14 include an Ethernet (registered trademark) interface. Examples of a usable network include a personal area network (PAN), a local area network (LAN), a campus area network (CAN), a metropolitan area network (MAN), a wide area network (WAN), a global area network (GAN), and an internetwork containing a combination thereof. The internetwork may be an intranet, may be an extranet, or may be the Internet.

Note that the determination program P for causing the processor 11 to carry out the determination method M1 may be stored in a computer-readable non-transitory tangible storage medium. This storage medium can be the secondary memory 13 or another storage medium. For example, a tape, a disk, a card, a semiconductor memory, a programmable logic circuit, or the like can be used as said another storage medium.

The present embodiment employs a configuration in which a single processor (the processor 11) is used to carry out the determination method M1. Note, however, that the present invention is not limited to this. That is, alternatively, employed may be a configuration in which a plurality of processors are used to carry out the determination method M1. In this case, the plurality of processors for carrying out the determination method M1 may be provided in a single computer and be configured to be communicable with each other via a bus or may be dispersedly provided in a respective plurality of computers and be configured to be communicable with each other via a network. For example, the following alternative aspects are also possible: an aspect in which processors included in a respective plurality of computers constituting a cloud server work together to carry out the determination method M1; and an aspect in which the processor 11 of the determination device 1 and a processor of the notification terminal 2 work together to carry out the determination method M1.

(Flow of Determination Method)

Figure 5:
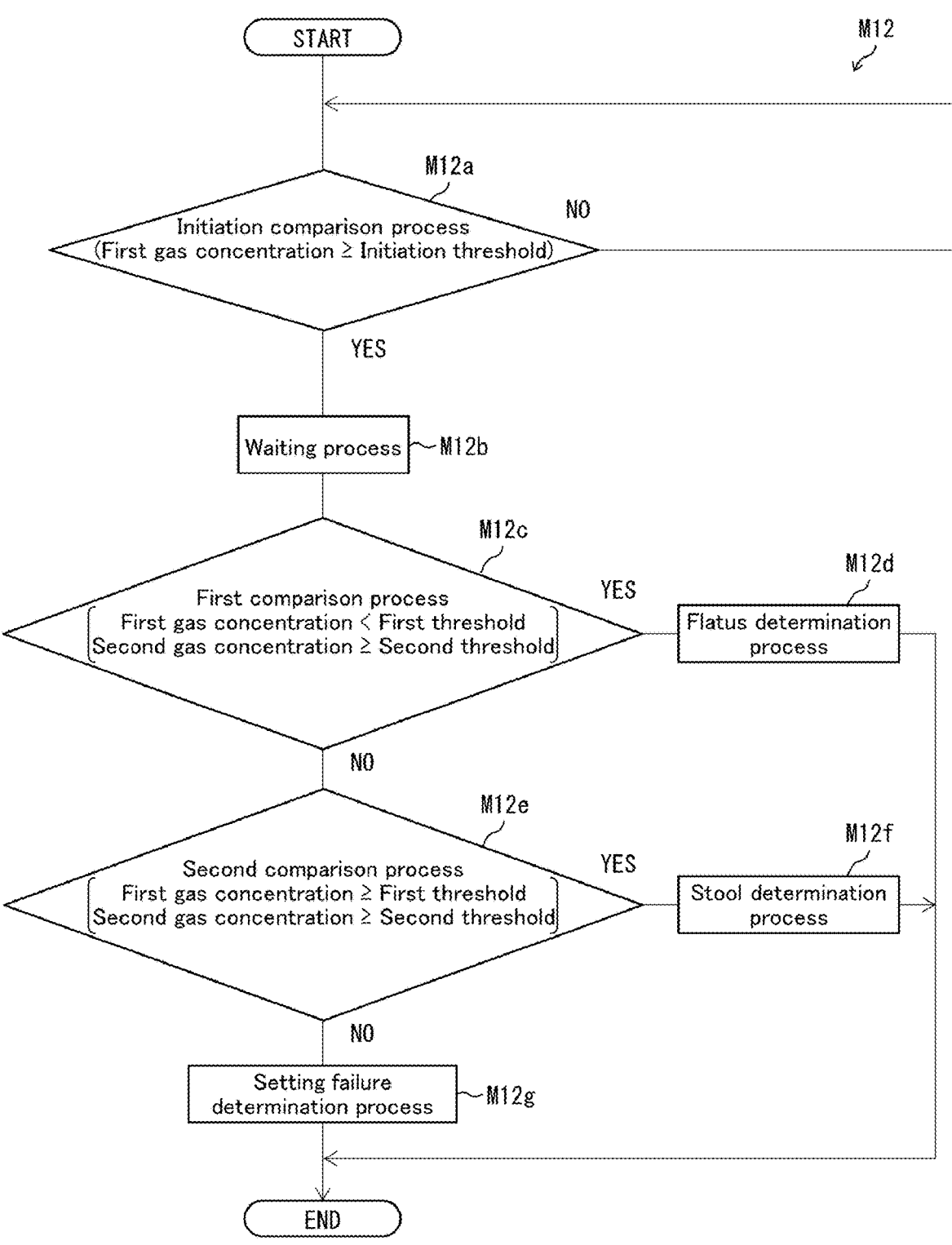
FIG. 5 is a flowchart showing a specific example of a determination process included in the determination method shown in FIG. 4.

With reference to FIGS. 4 and 5, the following will describe a flow of the determination method M1 carried out by the determination device 1.

FIG. 4 is a flowchart showing a flow of the determination method M1 carried out by the determination device 1 illustrated in FIG. 3. As illustrated in FIG. 4, the determination method M1 includes an acquisition process M11, a determination process M12, and a notification process M13. In the present embodiment, the acquisition process M11, the determination process M12, and the notification process M13 are carried out by the processor 11 of the determination device 1.

The acquisition process M11 is a process of acquiring a first gas concentration, which is a gas concentration detected by the first gas sensor 41, and a second gas concentration, which is a gas concentration detected by the second gas sensor 42. In the present embodiment, the processor 11 acquires, from a gas sensor(s), a gas concentration(s) detected by the gas sensor(s) via the communication interface(s) of the gas sensor(s) and the communication interface 14 of the determination device 1. However, the present invention is not limited to such a configuration. As an example, the processor 11 may acquire the first gas concentration and the second gas concentration by reading, from the secondary memory 13, the first gas concentration and the second gas concentration that are stored in the secondary memory 13.

The determination process M12 is a process of determining a type of excretion by the service user Ua by referring to the first gas concentration and the second gas concentration. A specific example of the determination process M12 will be described later with reference to another drawing.

Note that, the processor 11 may subject the gas concentrations acquired in the acquisition process M11 to preprocessing and carry out the determination process M12 with use of the gas concentrations subjected to the preprocessing. Examples of such preprocessing include: a scaling process, such as normalization and standardization; a filtering process, such as high-pass filtering and low-pass filtering; and an interpolation process, such as linear interpolation and spline interpolation.

The notification process M13 is a process of notifying the notification terminal 2 used by the service provider Ub of the type of excretion determined in the determination process M12. In the present embodiment, the processor 11 transmits a notification screen indicating the type of excretion determined, to the notification terminal 2 with use of the communication interface 14.

Specific Example of Determination Process

With reference to FIG. 5, the following will describe a specific example of the determination process M12. FIG. 5 is a flowchart showing a specific example of the determination process M12 included in the determination method M1 shown in FIG. 4.

As shown in FIG. 5, the determination process M12 can be constituted by, for example, an initiation comparison process M12*a*, a waiting process M12*b*, a first comparison process M12*c*, a flatus determination process M12*d*, a second comparison process M12*e*, a stool determination process M12*f*, and a setting failure determination process M12*g*. In the present embodiment, the initiation comparison process M12*a*, the waiting process M12*b*, the first comparison process M12*c*, the flatus determination process M12*d*, the second comparison process M12*e*, the stool determination process M12*f*, and the setting failure determination process M12*g* are carried out by the processor 11 of the determination device 1.

The initiation comparison process M12*a* is a process of comparing the first gas concentration with a predetermined initiation threshold. In a case where, in the initiation comparison process M12*a*, the first gas concentration is less than the initiation threshold (NO), the processes are repeated. That is, as long as the first gas concentration acquired in the acquisition process M11 is less than the initiation threshold, the acquisition process M11 and the initiation comparison process M12*a* are repeatedly carried out.

In a case where, in the initiation comparison process M12a, the first gas concentration has been determined to be not less than the initiation threshold (YES), the waiting process M12b is carried out. The waiting process M12b is a process of waiting for a predetermined time period T after the first gas concentration has become not less than the predetermined initiation threshold. In the present embodiment, the time period T has been set in advance by the service provider Ub with use of the notification terminal 2.

When the waiting process M12b has been completed, the first comparison process M12c is carried out. The first comparison process M12c is a process of comparing the first gas concentration with a predetermined first threshold and comparing the second gas concentration with a predetermined second threshold.

In a case where, in the first comparison process M12c, the first gas concentration is less than the first threshold, and the second gas concentration is not less than the second threshold (YES), the flatus determination process M12d is carried out. The flatus determination process M12d is a process of determining that a type of excretion by the service user Ua is flatus.

Note that, as a variation, in a case where, in the first comparison process M12c, the first gas concentration is less than the first threshold, the flatus determination process M12d may be carried out, regardless of whether or not the second gas concentration is not less than the second threshold. Also in such a variation, the same effect as that of the present embodiment is exerted.

In a case where a result of the determination in the first comparison process M12c is NO, the second comparison process M12e is carried out. The second comparison process M12e is a process of comparing the first gas concentration with the predetermined first threshold and comparing the second gas concentration with the predetermined second threshold.

In a case where, in the second comparison process M12e, the first gas concentration is not less than the first threshold, and the second gas concentration is not less than the second threshold (YES), the stool determination process M12f is carried out. The stool determination process M12f is a process of determining that a type of excretion by the service user Ua is a stool.

In a case where a result of the determination in the second comparison process M12e is NO, the setting failure determination process M12g is carried out. The setting failure determination process M12g is a process of determining that the time period T is not appropriately set, that is, that a failure of setting of the predetermined time period T has occurred.

Effect of the Present Embodiment

As described above, the determination device 1 in accordance with the present embodiment includes the at least one processor 11, the at least one processor 11 being configured to carry out the determination process M12 of determining a type of excretion by the subject Ua by referring to a first gas concentration and a second gas concentration, the first gas concentration being a gas concentration detected by the first gas sensor 41, and the second gas concentration being a gas concentration detected by the second gas sensor 42 which is disposed at a position farther from the subject Ua than a position at which the first gas sensor 41 is disposed.

According to such a configuration, the processor 11 refers to gas concentrations detected by the first gas sensor and the second gas sensor that are disposed at positions different from each other in distance from the subject Ua. Thus, it is possible to achieve a device that enables determination of a type of excretion by the subject Ua.

Further, in the present embodiment, in the determination process M12, at a point in time when a predetermined time period T has passed after the first gas concentration had become not less than a predetermined initiation threshold, the processor 11 is configured to: (i) determine, in a case where the first gas concentration is less than a predetermined first threshold, that the type of excretion by the subject Ua is flatus; and (ii) determine, in a case where the first gas concentration is not less than the first threshold, and the second gas concentration is not less than a predetermined second threshold, that the type of excretion by the subject Ua is a stool. Further, in the present embodiment, in the determination process M12, at a point in time when a predetermined time period T has passed after the first gas concentration had become not less than a predetermined initiation threshold, the processor 11 is configured to: (i) determine, in a case where the first gas concentration is less than a predetermined first threshold, and the second gas concentration is not less than a predetermined second threshold, that the type of excretion by the subject Ua is flatus; and (ii) determine, in a case where the first gas concentration is not less than the first threshold, and the second gas concentration is not less than the second threshold, that the type of excretion by the subject Ua is a stool.

According to each of such configurations, it is possible to achieve a technique in which the processor 11 enables accurate determination of whether a type of excretion by the subject Ua is a stool or flatus. When flatus by the subject Ua occurs, gas derived from the flatus diffuses from a hip of the subject Ua. This increases the second gas concentration. However, an increase in concentration of gas derived from flatus is temporary, and thus, in a case where the time period T is appropriately set, the first gas concentration presumably decreases after the time period T. When a stool by the subject Ua occurs, gas derived from the stool diffuses from a hip of the subject Ua. This increases the second gas concentration. An increase in concentration of gas derived from a stool is continuous, and thus, in a case where the time period T is appropriately set, the first gas concentration is presumably still high after the time period T. In the present embodiment, the first comparison process M12c and the second comparison process M12e are based on such principles.

Further, in the present embodiment, in the determination process M12, at a point in time when a predetermined time period T has passed after the first gas concentration had become not less than a predetermined initiation threshold, the processor 11 is configured to (iii) determine, in a case where the first gas concentration is not less than a predetermined first threshold, and the second gas concentration is less than a predetermined second threshold, that a failure of setting of the predetermined time period T has occurred.

According to such a configuration, it is possible to reduce the possibility of occurrence of erroneous determination due to inappropriate setting of the time period T. Thus, it is possible to reduce the possibility that treatment for a stool of a service user is delayed due to such erroneous determination. In a case of inappropriate setting of the time period T, that is, in a case where the time period T is excessively short or excessively long, after the time period T, the first gas concentration is still high, but the second gas concentration does not increase. In the present embodiment, the setting failure determination process M12g is based on such a principle.

Further, in the present embodiment, the processor 11 is configured to further carry out the notification process M13 of notifying the notification terminal 2 used by the service provider Ub of a result of the determination process M12.

According to such a configuration, since the service provider Ub is notified of a result of the determination, it is possible to achieve a device that enables reduction in burden of excretion management for the subject Ua on the service provider Ub.

Further, the determination method M1 in accordance with the present embodiment includes: the acquisition process M11 of the at least one processor 11 acquiring a first gas concentration and a second gas concentration, the first gas concentration being a gas concentration detected by the first gas sensor 41, the second gas concentration being a gas concentration detected by the second gas sensor 42 which is disposed at a position farther from a subject Ua than a position at which the first gas sensor 41 is disposed; and the determination process M12 of the at least one processor 11 determining a type of excretion by the subject Ua by referring to the first gas concentration and the second gas concentration.

According to such a configuration, the processor 11 refers to gas concentrations detected by the first gas sensor and the second gas sensor that are disposed at positions different from each other in distance from the subject Ua. Thus, it is possible to achieve a method that enables determination of a type of excretion by the subject Ua.

Further, the determination system S in accordance with the present embodiment includes: the first gas sensor 41; the second gas sensor 42 disposed at a position farther from a subject Ua than a position at which the first gas sensor 41 is disposed; and the determination device 1 configured to carry out the determination process M12 of determining a type of excretion by the subject Ua by referring to a first gas concentration and a second gas concentration, the first gas concentration being a gas concentration detected by the first gas sensor 41, the second gas concentration being a gas concentration detected by the second gas sensor 42.

According to such a configuration, it is possible to achieve a determination system S for determining a type of excretion by a subject Ua. The determination system S includes the first gas sensor 41 and the second gas sensor 42, both of which are gas sensors, and thus has a simple configuration, compared with a determination system of a conventional technique constituted by a combination of a gas sensor and a humidity sensor.

(Variation)

In the present embodiment, an aspect in which the determination method M1 is carried out by the determination device 1 is described, but the present invention is not limited to this. That is, the determination method M1 may be carried out by the relay terminal 3 or may be carried out by the notification terminal 2.

In a case where the relay terminal 3 carries out the determination method M1, the first gas sensor 41 and the second gas sensor 42 each transmit an output signal to the relay terminal 3, and then the relay terminal 3 transmits, to the determination device 1, a detection result that the relay terminal 3 itself has obtained. In this case, the determination device 1 does not carry out the determination method M1 and functions as a notification device for transmitting, to the notification terminal 2, a notification screen indicating the determination result obtained from the relay terminal 3.

In a case where the notification terminal 2 carries out the determination method M1, the first gas sensor 41 and the second gas sensor 42 each transmit an output signal to the relay terminal 3, and then the relay terminal 3 transmits, to the determination device 1, the output signals obtained from the gas sensors. The determination device 1 does not carry out the determination method M1 and functions as a relay device for transmitting, to the notification terminal 2, the output signals obtained from the relay terminal 3. In this case, the notification terminal 2 displays a notification screen including a determination result that the notification terminal 2 itself has obtained.

In the present embodiment, an aspect in which a type of excretion is determined to be either one of a stool or flatus is described, but the present invention is not limited to this. The type of excretion to be determined may be any combination of two or more types of excretion. Examples of such types of excretion to be determined include a stool, urine, and flatus.

In the present embodiment, an aspect in which the first gas sensor 41 is attached to the inside of underwear of the subject Ua, and the second gas sensor 42 is attached to the inside of upper garment is described, but the present invention is not limited to this. The first gas sensor 41 and the second gas sensor 42 each may be disposed at any position, provided that the second gas sensor 42 is disposed at a position farther from the subject Ua than a position at which the first gas sensor 41 is disposed. For example, a configuration may be employed in which the first gas sensor 41 is attached to the clothes of the subject Ua, and the second gas sensor 42 is attached to a side wall of a room in which the subject Ua is present.

In the present invention, an algorithm for determining a type of excretion in the determination process M12 is not limited to the algorithm of the specific example described above for the present embodiment. Examples of such an algorithm for determining a type of excretion include an algorithm in which used is a learned model subjected to machine learning with use of training data in which a type of excretion to be determined, a first gas concentration, and a second gas concentration are associated with each other; and an algorithm in which an actual value is used as a reference for comparison, wherein the actual value has been set on the basis of a correspondence between a type of each past excretion by a subject and a combination of a first gas concentration and a second gas concentration that have been detected in the past excretion.

In addition, in the present invention, a method for setting the predetermined time period T is not limited to the method in which the service provider Ub sets the time period T in advance. For example, the first gas sensor 41 and the second gas sensor 42 each may have a configuration of detecting a distance therebetween (for example, near field wireless communication), and the processor 11 may set the time period T with reference to the distance detected.

(Supplementary Note)

The present invention is not limited to the embodiments above, but can be altered by a skilled person in the art within the scope of the claims. The present disclosure also encompasses, in its technical scope, any embodiment derived by combining technical means disclosed in differing embodiments as appropriate.

The invention claimed is:

1. A determination device comprising at least one processor, the at least one processor being configured to carry out a determination process of determining a type of excretion by a subject by referring to a first gas concentration and a second gas concentration, the first gas concentration being a gas concentration detected by a first gas sensor, the second gas concentration being a gas concentration detected by a second gas sensor which is disposed at a position farther from the subject than a position at which the first gas sensor is disposed, wherein in the determination process, at a point in time when a predetermined time period has passed after the first gas concentration had become not less than a predetermined initiation threshold, the at least one processor is configured to:

(i) determine, in a case where the first gas concentration is less than a predetermined first threshold, and the second gas concentration is not less than a predetermined second threshold, that the type of excretion by the subject is flatus; and (ii) determine, in a case where the first gas concentration is not less than the first threshold, and the second gas concentration is not less than the second threshold, that the type of excretion by the subject is a stool.

2. The determination device according to claim 1, wherein, in the determination process, at a point in time when a predetermined time period has passed after the first gas concentration had become not less than a predetermined initiation threshold, the at least one processor is configured to (iii) determine, in a case where the first gas concentration is not less than a predetermined first threshold, and the second gas concentration is less than a predetermined second threshold, that a failure of setting of the predetermined time period has occurred.

3. The determination device according to claim 1, wherein the at least one processor is configured to further carry out a notification process of notifying a notification terminal used by a service provider of a result of the determination process.

4. A determination method comprising:

an acquisition process of at least one processor acquiring a first gas concentration and a second gas concentration, the first gas concentration being a gas concentration detected by a first gas sensor, the second gas concentration being a gas concentration detected by a second gas sensor which is disposed at a position farther from a subject than a position at which the first gas sensor is disposed; and a determination process of the at least one processor determining a type of excretion by the subject by referring to the first gas concentration and the second gas concentration, wherein

12 in the determination process, at a point in time when a predetermined time period has passed after the first gas concentration had become not less than a predetermined initiation threshold, the at least one processor:

(i) determines, in a case where the first gas concentration is less than a predetermined first threshold, and the second gas concentration is not less than a predetermined second threshold, that the type of excretion by the subject is flatus; and (ii) determines, in a case where the first gas concentration is not less than the first threshold, and the second gas concentration is not less than the second threshold, that the type of excretion by the subject is a stool.

5. A determination system comprising:

a first gas sensor;

a second gas sensor disposed at a position farther from a subject than a position at which the first gas sensor is disposed; and a determination device configured to carry out a determination process of determining a type of excretion by the subject by referring to a first gas concentration and a second gas concentration, the first gas concentration being a gas concentration detected by the first gas sensor, the second gas concentration being a gas concentration detected by the second gas sensor, wherein the determination device includes at least one processor, the at least one processor is configured to carry out the determination process of determining the type of excretion by the subject by referring to the first gas concentration and the second gas concentration, and in the determination process, at a point in time when a predetermined time period has passed after the first gas concentration had become not less than a predetermined initiation threshold, the at least one processor is configured to:

(i) determine, in a case where the first gas concentration is less than a predetermined first threshold, and the second gas concentration is not less than a predetermined second threshold, that the type of excretion by the subject is flatus; and (ii) determine, in a case where the first gas concentration is not less than the first threshold, and the second gas concentration is not less than the second threshold, that the type of excretion by the subject is a stool.

* * * * *